(12) United States Patent
Kadomura et al.

(10) Patent No.: US 8,791,957 B2
(45) Date of Patent: Jul. 29, 2014

(54) MEDICAL IMAGE DISPLAY DEVICE AND METHOD OF MEDICAL IMAGE DISPLAY

(75) Inventors: Takayuki Kadomura, Tokyo (JP); Takashi Shirahata, Tokyo (JP); Tetsuo Nakazawa, Tokyo (JP)

(73) Assignee: Hitachi Medical Corporation, Tokyo (JP)

(*) Notice: Subject to any disclaimer, the term of this patent is extended or adjusted under 35 U.S.C. 154(b) by 472 days.

(21) Appl. No.: 13/131,062

(22) PCT Filed: Dec. 3, 2009

(86) PCT No.: PCT/JP2009/070328
§ 371 (c)(1),
(2), (4) Date: May 25, 2011

(87) PCT Pub. No.: WO2010/064687
PCT Pub. Date: Jun. 10, 2010

(65) Prior Publication Data
US 2011/0261072 A1  Oct. 27, 2011

(30) Foreign Application Priority Data
Dec. 5, 2008 (JP) ................................ 2008-310790

(51) Int. Cl.
| | |
|---|---|
| *G09G 5/00* | (2006.01) |
| *A61B 8/08* | (2006.01) |
| *A61B 8/00* | (2006.01) |
| *G06T 15/08* | (2011.01) |
| *A61B 5/00* | (2006.01) |
| *A61B 6/03* | (2006.01) |
| *A61B 5/055* | (2006.01) |
| *A61B 6/00* | (2006.01) |

(52) U.S. Cl.
CPC ............... *A61B 5/055* (2013.01); *A61B 8/483* (2013.01); *A61B 8/00* (2013.01); *G06T 15/08* (2013.01); *A61B 5/7425* (2013.01); *A61B 6/032* (2013.01); *A61B 6/466* (2013.01)
USPC ............................ 345/619; 345/419; 345/440

(58) Field of Classification Search
USPC ................. 345/419, 619, 667, 440; 382/131; 600/407, 425
See application file for complete search history.

(56) References Cited

U.S. PATENT DOCUMENTS

| | | | |
|---|---|---|---|
| 2003/0153823 A1* | 8/2003 | Geiser et al. ................... | 600/407 |
| 2005/0119550 A1* | 6/2005 | Serra et al. ..................... | 600/407 |
| 2006/0238534 A1 | 10/2006 | Matsumoto | |
| 2009/0318800 A1* | 12/2009 | Gundel et al. ................. | 600/425 |
| 2011/0018871 A1* | 1/2011 | Shirahata ....................... | 345/419 |
| 2011/0164064 A1* | 7/2011 | Tanaka et al. .................. | 345/667 |
| 2013/0039560 A1* | 2/2013 | Goto .............................. | 382/131 |

FOREIGN PATENT DOCUMENTS

| | | | |
|---|---|---|---|
| JP | 2002-253545 | | 9/2002 |
| JP | 2004-194782 | | 7/2004 |
| JP | 2006-302103 | | 11/2006 |
| JP | 2008-100107 | | 5/2008 |
| WO | WO-2010/024331 | * | 4/2010 |

OTHER PUBLICATIONS

Fujimura, Kaori, JP 2002-253545, English Machine Translation of "Medical Image Interpretation Recroding Device, Medical Image Interpretation Supporting Device and System, Medical Image Interpretation Recording Program, Recording MEdium for This Program, and Medical Image Interpretation Support Processing Program".*
Tanaka et al, WO2010024331, PCT JP2009/0646958, English Machine Translation of "Image Processing Device and Method for Processing Image", 2009.*
International Search Report in PCT/JP2009/070328.

* cited by examiner

*Primary Examiner* — Chante Harrison
(74) *Attorney, Agent, or Firm* — Cooper & Dunham LLP

(57) ABSTRACT

In a medical image display device for displaying a hollow organ of an examinee as a panoramic image, an operator is enabled to easily determine whether display of an observation site on the panoramic image is correct or not. The medical image display device having panoramic image creating means configured to create a panoramic image of a hollow organ of an examinee and display means configured to display the panoramic image includes false image probability calculating means configured to calculate a false image probability of a position in the panoramic image in accordance with the position concerned, and control means configured to display the false image probability in association with the panoramic image. Furthermore, the medical image display device having panoramic image creating means configured to create a panoramic image of a hollow organ of an examinee and display means configured to display the panoramic image includes false image probability calculating means configured to calculate a false image probability of a position in the panoramic image in accordance with the position concerned, and control means configured to display the panoramic image on the basis of the false image probability.

2 Claims, 18 Drawing Sheets

MEDICAL IMAGE DISPLAY DEVICE AND METHOD OF MEDICAL IMAGE DISPLAY

TECHNICAL FIELD

The present invention relates to a medical image display device for displaying a hollow organ of an examinee as a panoramic image, and particularly to a technique of calculating a false image probability in accordance with a position in the panoramic image and presenting the false image probability to an operator.

BACKGROUND ART

A method of displaying the inner cavity of a hollow organ such as a blood vessel, a large bowel or the like in a virtual endoscope display style by using an image scanned by using a medical image diagnosis device such as an X-ray CT device, an MRI device or the like is useful to observe the shape of the inner wall of the hollow organ. Particularly, in a large bowel region, it is possible to observe the inner wall of the large bowel without inserting an endoscope into a body. Therefore, this method is a less invasive and much attention is paid to this method as an examination method imposing little mental and physical burden on an examinee.

In addition to a virtual endoscope image created by the method described above, an MPR (Multi Planner Reconstruction) image, etc. are also known as an image used when a large bowel is examined by using the medical image diagnosing apparatus, and a panoramic image has been proposed as a characteristic display image (patent document 1). The panoramic image is an image which is displayed like a specimen as if a hollow organ is cut open in a long axis direction, and this has been expected as a method of reducing a burden of interpretation of radiogram because this method makes it possible to command a panoramic view of the inner wall of the hollow organ. Particularly when the inner wall of a large bowel is observed, the panoramic image makes it possible to observe the inner wall of the large bowel on plane, and thus makes it easy to detect polyp or the like existing between folds of the large bowel which may be overlooked in the virtual endoscope image.

The panoramic image can be created by radiating a virtual light beam in a radial direction from each point on the center line of the inner cavity of a large bowel region, projecting a pixel value or reflection light at an impinging portion of the virtual light beam against the inner wall of the large bowel onto the inner surface of one linear hollow cylindrical model, cutting open the cylindrical model in the long axis direction thereof and unrolling the inner surface of the cylindrical model onto a plane.

PRIOR ART DOCUMENT

Patent Document

Patent Document 1: Japanese Patent No. 03,627,066

SUMMARY OF THE INVENTION

Problem to be solved by the Invention

There is a case where the panoramic image does not correctly represent the shape of the inner wall at some positions of the hollow organ. For example, the large bowel region contains bent portions such as a portion from an ascending colon to a transverse colon, a portion from the transverse colon to a descending colon, an sigmoid colon, etc., and when a hollow cylinder is cut open and unrolled onto a plane, distortion occurs in images of the bent portions. Specifically, the image of a bent portion extends in the long axis direction of the hollow organ at the inside of the bent portion concerned, and conversely shrinks at the outside of the bent portion concerned. Such distortion may cause erroneous diagnosis in image diagnosis. For example, there is a case where a spherical polyp existing at a bent portion is displayed with extending or shrinking in the long axis direction of the large bowl, so that the spherical polyp looks like a fold. Conversely, there is a case where a fold at the outside of a bent portion is displayed with extending and thus looks like a polyp.

An operator must observe a panoramic image in consideration of a case where the panoramic image does not correctly display the shape of the inner wall of a hollow organ at some positions of the hollow organ. However, by merely observing the panoramic image, it is difficult to determine whether display of an observation site is correct or not.

The present invention has been implemented in view of such a situation, and has an object to enable an operator to easily determine whether display of an observation site on a panoramic image is correct or not in a medical image display device for displaying a hollow organ of an examinee as a panoramic image.

Means of Solving the Problem

In order to attain the above object, a medical image display device according to the present invention having panoramic image creating means configured to create a panoramic image of a hollow organ of an examinee, and display means configured to display the panoramic image is characterized by comprising false image probability calculating means configured to calculate a false image probability of a position in the panoramic image in accordance with the position concerned, and control means configured to display the false image probability in association with the panoramic image.

Furthermore, according to the present invention, a medical image display device having panoramic image creating means configured to create a panoramic image of a hollow organ of an examinee, and display means configured to display the panoramic image is characterized by comprising false image probability calculating means configured to calculate a false image probability of a position in the panoramic image in accordance with the position concerned, and control means configured to display the panoramic image on the basis of the false image probability.

Still furthermore, according to the present invention, a medical image display method having a panoramic image creating step that creates a panoramic image of a hollow organ of an examinee, and a display step that displays the panoramic image is characterized by comprising a false image probability calculating step that calculates a false image probability of a position in the panoramic image in accordance with the position concerned, and a control step that displays the false image probability in association with the panoramic image.

Still furthermore, a medical image display method having a panoramic image creating step that creates a panoramic image of a hollow organ of an examinee and a display step that displays the panoramic image is characterized by comprising a false image probability calculating step that calcu-lates a false image probability of a position in the panoramic image in accordance with the position concerned, and a control step that displays the panoramic image on the basis of the false image probability.

Effect of the Invention

According to the present invention, in the medical image display device for displaying the panoramic image of the hollow organ of the examinee, the operator can easily determine whether the display of the observation site on the panoramic image is correct or not. The operator can easily determine whether the display of the observation site on the panoramic image is correct or not, whereby erroneous diagnosis in image diagnosis based on the panoramic image can be reduced.

MODES FOR CARRYING OUT THE INVENTION

Figure 1:
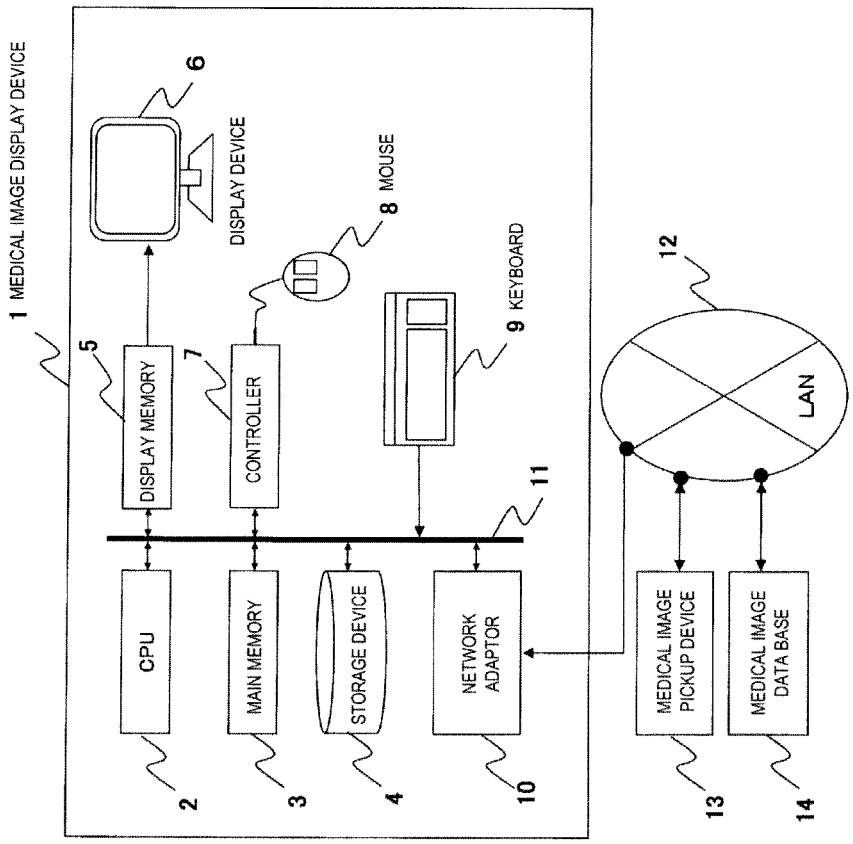
FIG. 1 is a diagram showing a hardware construction of a medical image display device according to the present invention.

A preferred embodiment of a medical image display device according to the present invention will be described with reference to the accompanying drawings. In the following description and the accompanying drawings, constituent elements having the same functional constructions are represented by the same reference numerals, and the duplicative description thereof is omitted.

FIG. 1 is a diagram showing the hardware construction of a medical image display device 1. The medical image display device 1 is configured to have CPU (Central Processing Unit) 2, a main memory 3, a storage device 4, a display memory 5, a display device 6, a mouse 8 and a keyboard 9 connected to a controller 7, and a network adaptor 10 which are connected to one another through a system bus 11. The medical image display device 1 is connected to a medical image scanning apparatus 13 and a medical image database 14 through a network 12.

CPU 2 is a device for controlling the operation of each constituent element. CPU 2 loads, into the main memory 3, a program and data necessary for execution of the program which are stored in the storage device 4, and executes the program. The storage device 4 is a device for storing medical image information scanned by the medical image scanning apparatus 13. The medical image information is obtained from the medical image scanning apparatus 13 or the medical image data base 14 through the network 12 such as LAN (Local Area Network) or the like. The storage device 4 stores programs to be executed by CPU 2 and data necessary to execute the programs. The main memory 3 stores the programs to be executed by CPU 2 and a progress status of operation processing.

The mouse 8 and the keyboard 9 are operating devices with which an operator instructs the medical image display device 1 to operate. The mouse 8 may be another pointing device such as a track pad, a trackball or the like. The display memory 5 stores display data to be displayed on the display device 6 such as a liquid crystal display, CRT (Cathode Ray Tube) or the like. The controller 7 detects a state of the mouse 8 to detect a position of a mouse pointer on the display device 6, and outputs a detection signal to CPU 2. The network adaptor 10 serves to connect the medical image display device 1 to the network 12 such as LAN, a telephone line, the Internet or the like.

The medical image scanning apparatus 13 is a device for obtaining the medical image information such as a tomographic image, etc. of an examinee. The medical image scanning apparatus 13 is, for example, an MRI device, an X-ray CT device or an ultrasonic diagnosing apparatus. The medical image data base 14 is a data base system for storing the medical image information scanned by the medical image scanning apparatus 13.

CPU 2 executes the following method to create a panoramic image of a hollow organ, and the created panoramic image is displayed on the display device 6. The panoramic image has a site which is not correctly displayed in accordance with a position of the hollow organ, and thus an operator must observe the panoramic image while considering which site in the panoramic image is not correctly displayed. However, by merely observing the panoramic image, it is difficult to determine whether display of an observed site is correct or not.

Therefore, according to the present invention, in accordance with a position in the panoramic image, a false image probability of the position concerned, that is, a degree at which a display of the position concerned is not correct is calculated, and the calculated false image probability is displayed on the display device 6 in association with the panoramic image, or the panoramic image is displayed on the display device 6 on the basis of the calculated false image probability.

A bending portion of the hollow organ, for example, a sigmoid colon of a large bowel region or the like is contained as a site having a high false image probability in the panoramic image. The false image probability increases as a degree of bending, that is, a bending degree in a long axis direction of the hollow organ is larger.

(First Embodiment)

Figure 2:
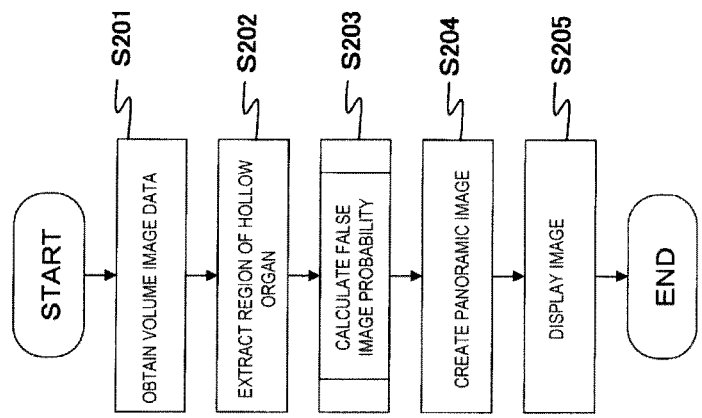
FIG. 2 is a diagram showing the flow of processing according to a first embodiment.

FIG. 2 is a diagram showing the flow of processing in which a false image probability of a position in a panoramic image calculated in accordance with the position concerned is displayed in association with the panoramic image or the panoramic image is displayed in accordance with the calculated false image probability. Each step of FIG. 2 will be described hereunder in detail.

(Step S201)

CPU 2 obtains volume image data of an examinee from the medical image scanning apparatus 13 or the medical image data base 14 through the network 12. Here, the volume image data correspond to several to several hundreds of tomographic images obtained by scanning images of the examinee, and the volume image data are constructed by continuously arranging these tomographic images in some direction, for example, in a direction vertical to a tomographic plane.

(Step S202)

Figure 3:
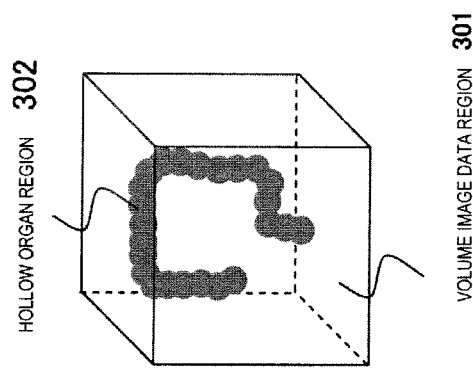
FIG. 3 is a diagram showing an example in which a hollow organ region is extracted from volume image data.

CPU 2 extracts a hollow organ region from the volume image data obtained in step S201. An extraction method based on threshold value processing using an upper limit value and a lower limit value of pixel values corresponding to a hollow organ as an extraction target, a publicly-known region growing method (Region Growing method, etc.) are known as a method of extracting a region. CPU 2 executes processing of erecting a flag at an extracted region, etc. to enables the extracted region to be discriminable from other regions. FIG. 3 shows an example in which a large bowel is extracted as the hollow organ from a volume image data region 301, and a flag is erected at the extracted region.

The extraction method of the hollow organ region and a data format of an extraction result used in this embodiment are not limited to the above method, and any method may be used insofar as it can output the extraction result to a processing step at the rear stage. In the description of this embodiment, for simplification, a format for erecting a flag at a coordinate on the extracted region as shown in FIG. 3 is adopted as the data format of the extraction result.

(Step S203)

Figure 4:
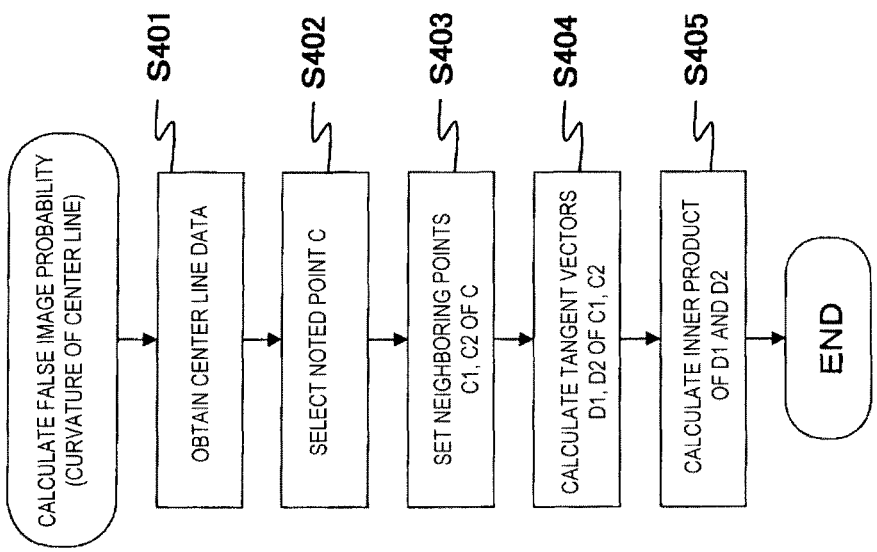
FIG. 4 is a diagram showing an example of the flow of processing of calculating a false image probability.

CPU 2 calculates a false image probability on the basis of the extraction result in step S202. FIG. 4 shows a procedure of determining a degree of bending in the long axis direction of the hollow organ as the false image probability as an example of the flow of processing of calculating the false image probability, and each of steps will be described hereunder.

(Step S401)

Figure 5:
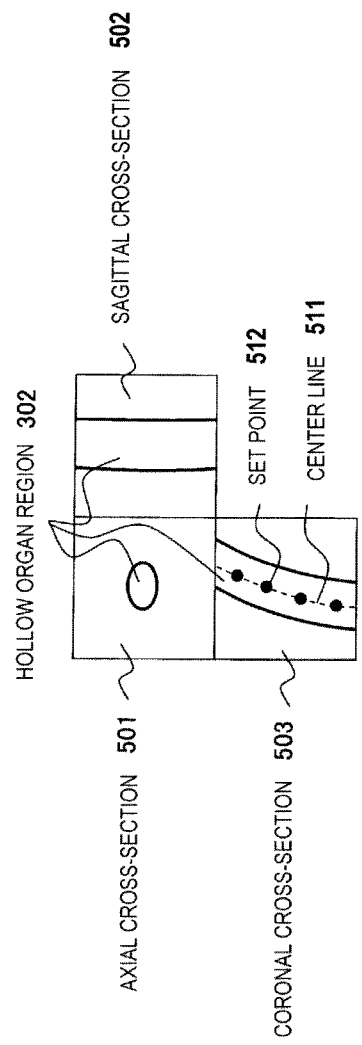
FIG. 5 is a diagram for supplemental explanation of a method of obtaining center line data.

CPU 2 determines the center line of the hollow organ, and obtains coordinate data of the determined center line. A method of geometrically determining the center line by thinning the hollow organ and a method of determining the center line from a specified point in the hollow organ region according to a publicly-known deepest part searching method are known as a method of determining the center line. Furthermore, there are known a method of setting a manually set free curve as the center line from MPR (Multi Planner Reconstruction) images of an axial cross-section 501, a sagittal cross-section 502 and a coronal cross-section 503 by operator's operation of the mouse 8 as shown in FIG. 5, a method of determining a curved line passing through plural set points 512 set by the operator according to spline interpolation or the like and setting this curved line as the center line, etc.

CPU 2 treats a determined center line 511 as an aggregate of points, sets plural points Cn at equal intervals on the center line 511 and holds a coordinate of each point Cn in the main memory 3, thereby obtaining the coordinate data of the center line.

(Step S402)

CPU 2 selects a noted point C from the plural points Cn as a target site for determining the degree of bending in the long axis direction of the hollow organ.

(Step S403)

Figure 6:
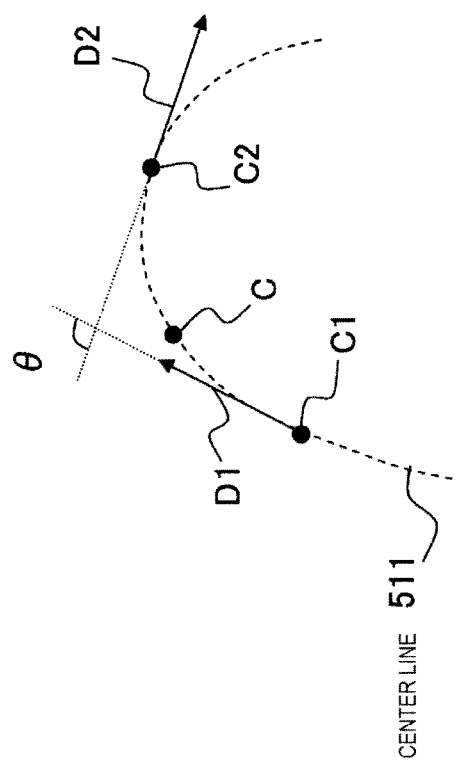
FIG. 6 is a diagram for supplemental explanation of the procedure of obtaining a bending degree at a noted point C.

Points which are located as neighboring points at front and rear sides of the noted point C selected in step S402 so as to be far away from the noted point C at fixed distances, for example, pints C1 and C2 adjacent to C are set as tangent vector calculation points by CPU 2 (see FIG. 6).

(Step S404)

CPU 2 calculates tangent vectors D1 and D2 of the center line 511 at the points C1 and C2.

(Step S405)

By using (expression 1), an inner product P of the tangent vectors D1 and D2 is calculated as curvature at the noted point C, and it is set as the degree of bending in the long axis direction of the hollow organ.

$$P = D1 \cdot D2 \qquad \text{(expression 1)}$$

In the flow of the processing of FIG. 4, the inner product P of the tangent vectors D1 and D2 is calculated as the curvature at the noted point C. However, an angle $\theta$ determined by using (expression 2) may be set as the degree of bending in the long axis direction of the hollow organ.

$$\theta = \cos^{-1}(D1 \cdot D2/(|D1||D2|)) \qquad \text{(expression 2)}$$

Figure 7:
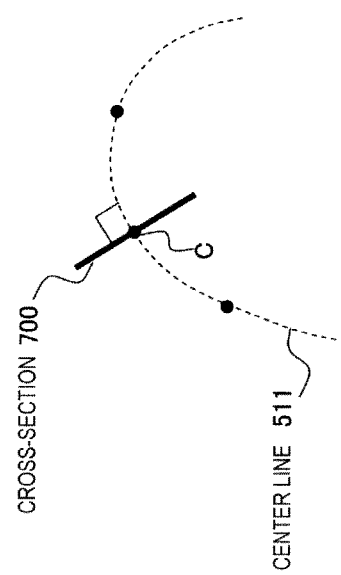
FIG. 7 is a diagram for supplemental explanation of a cross-section perpendicular to the center line.
Figure 8:
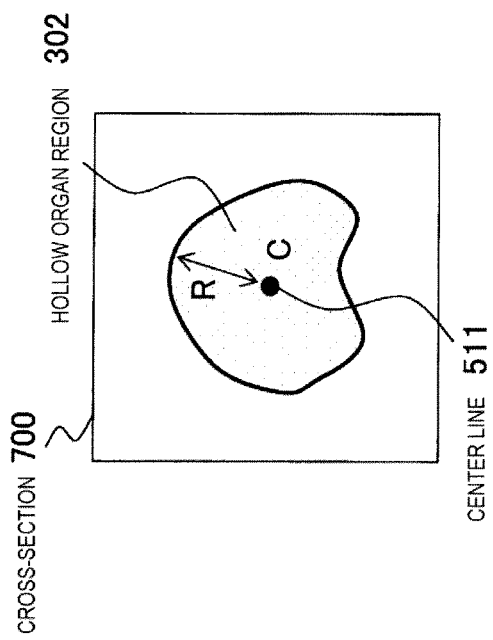
FIG. 8 is a diagram for supplemental explanation of the inner cavity of a hollow organ on a cross-section perpendicular to the center line.

Furthermore, the product between the inner product P and a radius R (see FIG. 8) of the inner cavity of the hollow organ on a cross-section 700 perpendicular to the center line 511 at the noted point C as shown in FIG. 7 maybe set as the degree of bending in the long axis direction. A degree of distortion in the panoramic image which is caused by the bending in the long axis direction of the hollow organ increases as the radius R of the inner cavity of the hollow organ is larger, and thus the false image probability can be more accurately determined by multiplying the radius R.

Figure 9:
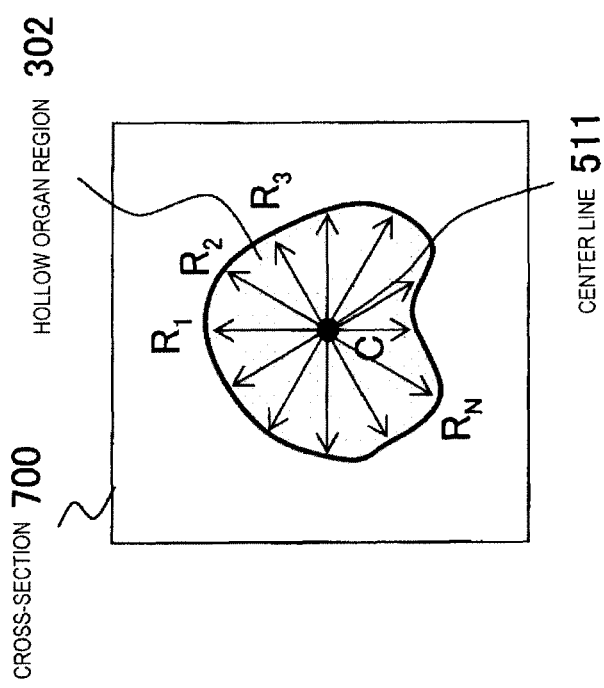
FIG. 9 is a diagram for supplemental explanation of an example of a method of determining a radius R of the inner cavity of the hollow organ.

The radius R of the inner cavity of the hollow organ may be determined as an average value of a distance $R_1, R_2, R_3 \ldots, R_N$ at each angle from the noted point C on the center line 511 to the inner wall of the hollow organ as shown in FIG. 9.

Figure 10:
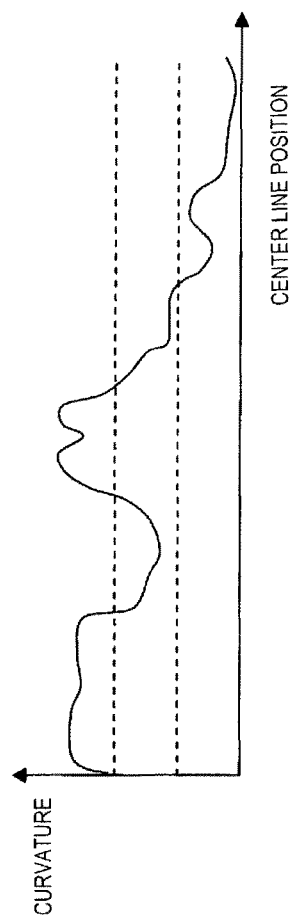
FIG. 10 shows an example of a graph of curvature and a center line position.

The degree of bending in the long axis direction of the hollow organ determined in this step is stored in the main memory 3 or the storage device 4 in association with each point on the center line 511. By storing the degree of bending and each point on the center line 511 in association with each other, whereby a graph of the curvature and the center line position as the position on the center line 511 in the long axis direction of the hollow curvature as shown in FIG. 10 can be created.

(Step S204)

CPU 2 creates a panoramic image for the hollow organ region extracted in step S202. The creation of the panoramic image may be performed by using, for example, the method described in the Patent Document 1. Here, a method of creating the panoramic image will be described with reference to FIG. 11.

(1) On the cross-section 700 perpendicular to the center line 511, plural virtual light beams 1100 are set from the noted point C on the center line 511 in the radial direction as shown in FIG. 11(a). At this time, it is preferable that angles between the respective virtual light beams are set to be equal to one another.

(2) Points $B_1, B_2, B_3, B_4, \ldots, B_N$ on the inner wall of the hollow organ are searched with scanning the virtual light beams 1100 while referring to the data of the region of the hollow organ extracted in step S202.

Figure 11:
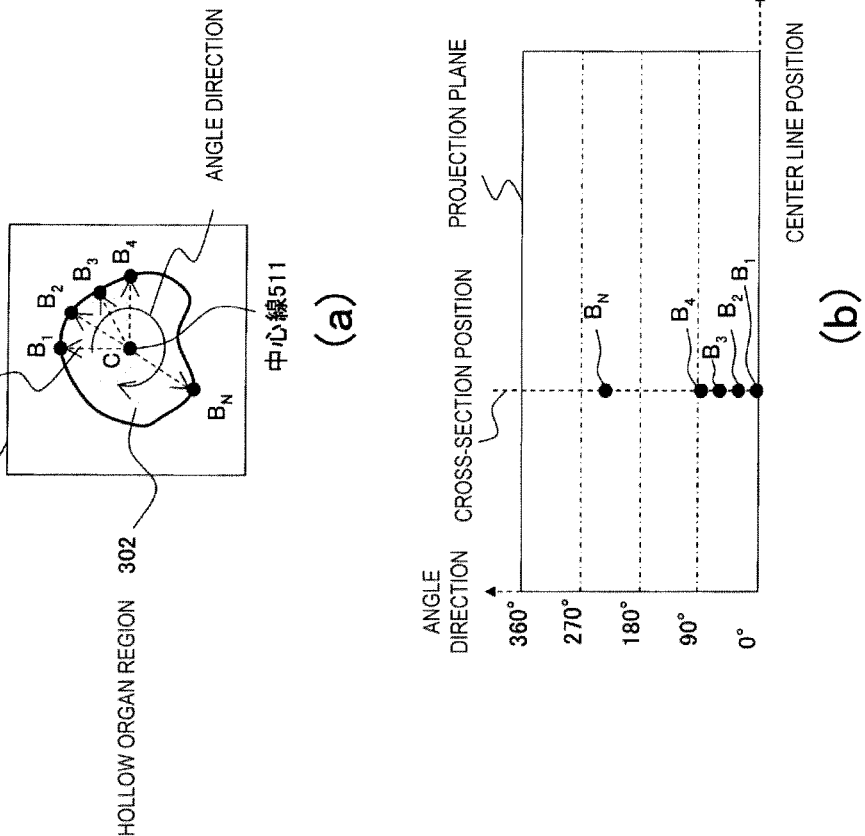
FIG. 11 is a diagram for supplemental explanation of the procedure of creating a panoramic image.

(3) The volume image data obtained in step S201 are associated with the points $B_1, B_2, B_3, B_4, \ldots, B_N$ on the inner wall of the hollow organ. As shown in FIG. 11(b), the associated image data are projected onto a projection plane on which the vertical axis represents the angle direction shown in FIG. 11(*a*) and the horizontal axis represents the center line position as the position on the center line 511 in the long axis direction of the hollow organ.

The processing (1) to (3) described above is executed by CPU 2 while the center line position is changed, thereby creating a panoramic image.

(Step S205)

CPU 2 displays the false image probability of each center line position calculated in step S203 in association with the panoramic image created in step S204 or displays the panoramic image in accordance with the false image probability. A display example will be described hereunder. In the following display example, the curvature which is one degree of bending in the long axis direction of the hollow organ is set as the false image probability.

DISPLAY EXAMPLE 1

Figure 12:
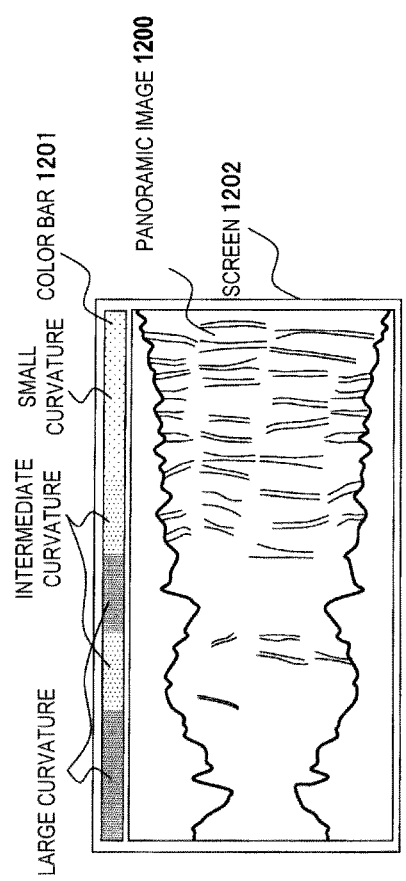
FIG. 12 is a diagram showing a display example 1.

FIG. 12 shows a display example. In this display example, a panoramic image 1200 and a color bar 1201 are displayed on a screen 1202 of the display device 6. A different color is allocated to the color bar 1201 every center line position, and a different color is allocated in accordance with the curvature determined every center line position in step S203. For example, at a large-curvature position, distortion in the panoramic image increases and thus a red color is allocated to promote an operator to pay his/her attention. At a small-curvature position, distortion in the panoramic image does not increase and thus a blue color is allocated, and a yellow color is allocated at an intermediate-curvature position.

By displaying the panoramic image as described above, the operator can know which observation site on the panoramic image has a large curvature, that is, has a high false image probability, and thus erroneous diagnosis of image diagnosis based on the panoramic image can be reduced.

DISPLAY EXAMPLE 2

Figure 13:
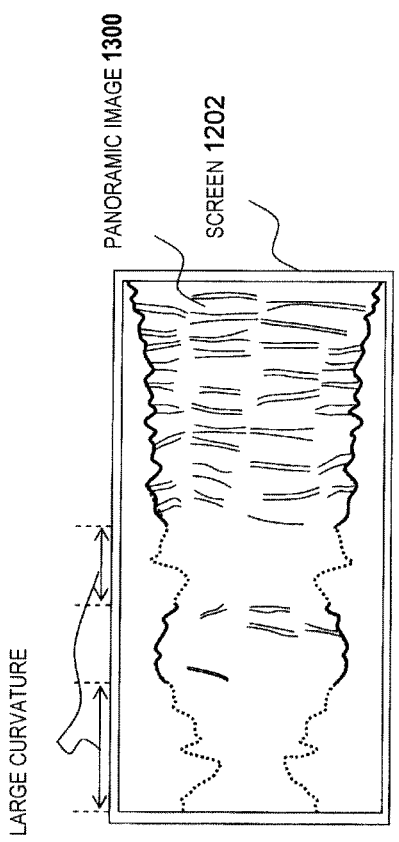
FIG. 13 is a diagram showing a display example 2.

This display example is shown in FIG. 13. In this display example, a panoramic image 1300 which is partially different in transparency is displayed on the screen 1202 of the display device 6. A dashed line portion in the panoramic image 1300 represents a portion which is displayed with the transparence being varied. The transparence of the panoramic image 1300 is varied in accordance with the curvature. High transparence is set at a large-curvature position at which the distortion in the panoramic image increases, and low transparence is set at a small-curvature position.

By displaying the panoramic image as described above, the operator can concentrically observe a small-curvature site on the panoramic image, that is, a site having a low false image probability, and thus erroneous diagnosis of image diagnosis based on the panoramic image can be reduced.

DISPLAY EXAMPLE 3

Figure 14:
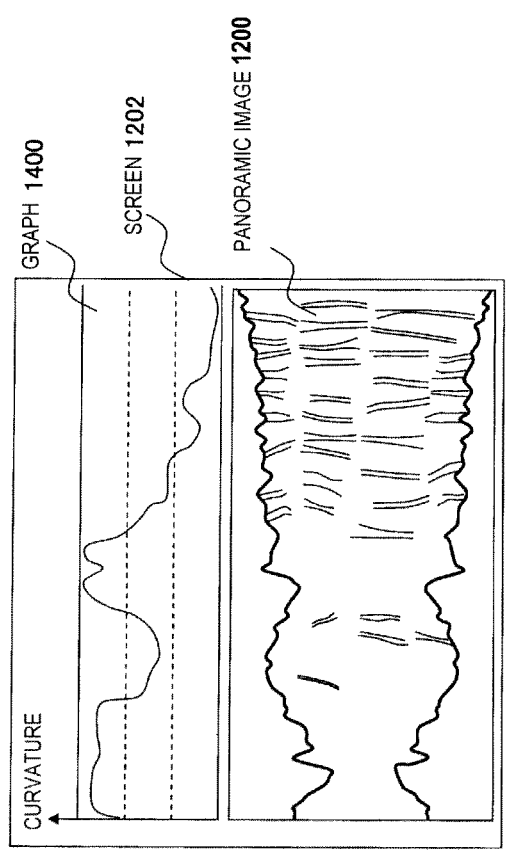
FIG. 14 is a diagram showing a display example 3.

FIG. 14 shows this display example. In this display example, the panoramic image 1200 and a graph 1400 are displayed to be arranged on the screen 1202 of the display device 6. The graph 1400 is the same as shown in FIG. 10, and it represents the relationship between the curvature and the center line position.

By displaying the panoramic image as described above, the operator can know which observation site on the panoramic image has a large curvature, that is, has a high false image probability, and thus erroneous diagnosis of image diagnosis based on the panoramic image can be reduced.

DISPLAY EXAMPLE 4

In the display examples 1 to 3, the curvature as the false image probability is treated as a continuous value to display the panoramic image. However, threshold-value determination maybe performed on the curvature as the false image probability in step S205 to display the panoramic image on the basis of a result of the threshold value determination. By displaying the panoramic image on the basis of the result of the threshold-value determination, a site which the operator should observe and a site which the operator should not observe can be easily discriminated from each other.

Figure 15:
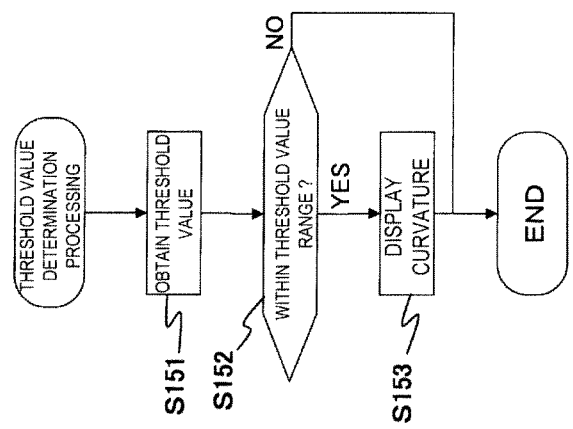
FIG. 15 is a diagram showing an example of the flow of processing of determining a threshold value.

FIG. 15 is a diagram showing an example of the flow of the processing of the threshold-value determination. Each step of FIG. 15 will be described hereunder.

(Step S151)

Figure 16:
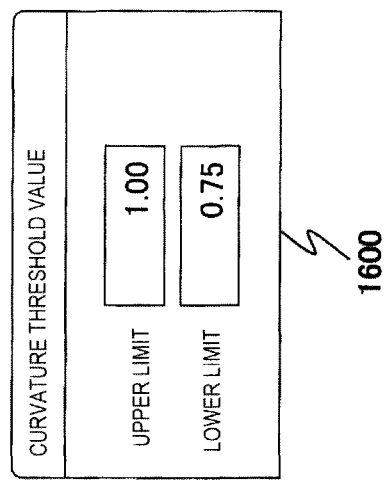
FIG. 16 is a diagram showing an example of a screen for setting the threshold value.

CPU 2 obtains a threshold value. The obtained threshold value may be a value pre-stored in the storage device 4 or an upper limit value and/or a lower limit value which is set through a threshold-value setting screen 1600 shown in FIG. 16 by the operator.

(Step S152)

CPU 2 compares the threshold value obtained in step S151 with the curvature determined every center line position in S203, and determines whether the curvature is within a threshold value range or not. When the curvature is within the threshold-value range as a result of the determination, the processing goes to step S153, and when the curvature is not within the range, the processing is finished.

(Step S153)

Figure 17:
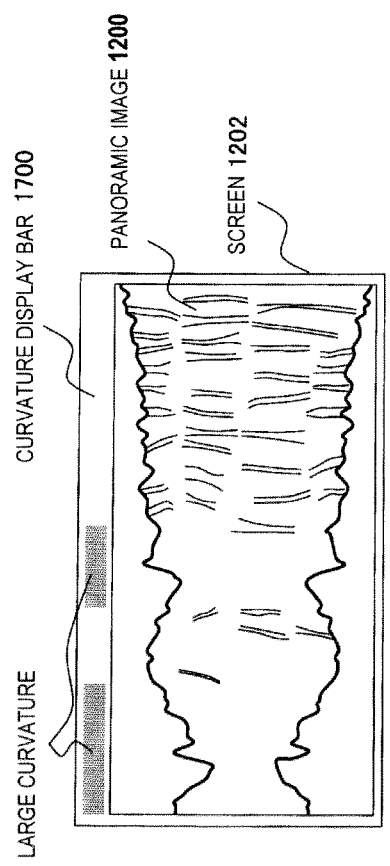
FIG. 17 is a diagram showing a display example 4.

CPU 2 displays the curvature on the screen 1202 of the display device 6 together with the panoramic image 1200. FIG. 17 shows a display example of this step. In this display example, a curvature display bar 1700 is displayed on the screen 1202 together with the panoramic image 1200. With respect to the curvature display bar 1700, a bar is displayed at a portion where the curvature is within the threshold-value range, and for example, a bar is displayed at a portion where the curvature is larger than the threshold value obtained in step S151.

By displaying the panoramic image as described above, the operator can know which observation site on the panoramic image has a high false image probability, and thus the erroneous diagnosis of the image diagnosis based on the panoramic image can be reduced.

DISPLAY EXAMPLE 5

Figure 18:
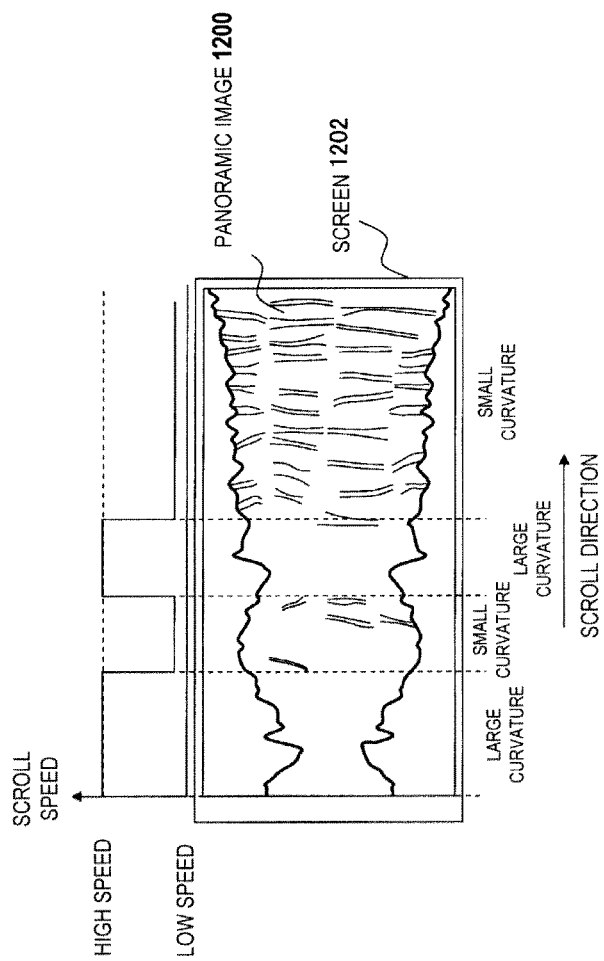
FIG. 18 is a diagram showing a display example 5.

FIG. 18 shows this display example. In this display example, the panoramic image 1200 is scroll-displayed on the screen 1202 of the display device 6. In FIG. 18, the scroll direction is set to the direction from left to right, however, it may be set to the opposite direction. In the scroll-display of this display example, the panoramic image 1200 is scroll-displayed while a scroll speed for a site at which the curvature is determined to be within the threshold-value range in the threshold-value determination shown in FIG. 15 is set to a high speed, and a scroll speed for a site at which the curvature is determined to be out of the threshold-value range is set to a low speed. From the viewpoint of easiness of observation, it is preferable that the curvature of the centerline position displayed at the center portion in the lateral direction of the screen 1202 is used as a target for the threshold-value determination.

By displaying the panoramic image as described above, the operator can concentrically observe a small-curvature site on the panoramic image, that is, a site having a low false image probability, and thus the erroneous diagnosis of the image diagnosis based on the panoramic image can be reduced.

The display examples of the panoramic image have been described by using the display examples 1 to 5. However, the present invention is not limited to these display examples, and any device maybe used insofar as it presents a false image probability of an observation site on a panoramic image to an operator in a medical image display device for displaying a hollow organ of an examinee as a panoramic image.

For example, when the panoramic image which is partially different in transparence as described with reference to the display example 2 is displayed, only a site at which the curvature is within the threshold-value range may be transparently displayed on the basis of the result of the threshold-value determination processing described with reference to FIG. 15.

Furthermore, when the scroll-display described with reference to the display example 5 is performed, the scroll-speed may be continuously varied in accordance with the value of the curvature.

Description Of Reference Numerals

1 medical image display device, 2 CPU, 3 main memory, 4 storage device, 5 display memory, 6 display device, 7 controller, 8 mouse, 9 keyboard, 10 network adaptor, 11 system bus, 12 network, 13 medical image scanning apparatus, medical image data base, 301 volume image data region, 302 hollow organ region, 501 axial cross-section, 502 sagittal cross-section, 503 coronal cross-section, 511 center line, 512 setting point, 700 cross-section, 1100 virtual light beam, 1200 panoramic image, 1201 color bar, 1202 screen, 1300 panoramic image, 1400 graph, 1600 threshold value setting screen, 1700 curvature display bar.

The invention claimed is:

1. A medical image display device comprising:
   panoramic image creating means configured to create a panoramic image of a hollow organ of an examinee;
   display means configured to display the panoramic image;
   false image probability calculating means configured to calculate a false image probability of a position in the panoramic image in accordance with the position concerned; and
   control means configured to create a graph of the false image probability and a center line position of the hollow organ, and to display the panoramic image and the graph in association with the center line position, on the display means.

2. A medical image display method performed by a medical image display device, the medical image display method comprising:
   a panoramic image creating step that creates a panoramic image of a hollow organ of
   an examinee;
   a display step that displays the panoramic image;
   a false image probability calculating step that calculates a false image probability of a position in the panoramic image in accordance with the position concerned; and
   a control step, performed by the medical image display device, that creates a graph of the false image probability and a center line position of the hollow organ and causes the panoramic image and the graph to be displayed in association with the center line position.

* * * * *